United States Patent [19]   [11] Patent Number: 5,969,182
Greindl et al.   [45] Date of Patent: Oct. 19, 1999

[54] PREPARATION OF SUBSTITUTED GUANIDINE DERIVATIVES

[75] Inventors: Thomas Greindl, Bad Dürkheim; Günter Scherr, Ludwigshafen; Rolf Schneider, Mannheim; Klaus Mundinger, Limburgerhof, all of Germany

[73] Assignee: BASF Aktiengesellschaft, Ludwigshafen, Germany

[21] Appl. No.: 09/179,463

[22] Filed: Oct. 27, 1998

[30] Foreign Application Priority Data

Nov. 4, 1997 [DE] Germany .................... 197 48 694

[51] Int. Cl.[6] .................................................. C07C 249/02
[52] U.S. Cl. ............................................ 562/560; 564/241
[58] Field of Search ............................... 562/560; 564/241

[56] References Cited

U.S. PATENT DOCUMENTS

| | | | |
|---|---|---|---|
| 4,421,602 | 12/1983 | Brunnmueller et al. ............... | 162/168 |
| 4,774,285 | 9/1988 | Pfohl et al. .............................. | 525/60 |
| 4,880,497 | 11/1989 | Pfohl et al. ............................. | 162/135 |
| 4,978,427 | 12/1990 | Pfohl et al. ............................. | 162/168 |
| 5,719,319 | 2/1998 | Weiss et al. ............................ | 562/560 |

FOREIGN PATENT DOCUMENTS

| | | |
|---|---|---|
| 78077364 | 6/1978 | Japan . |
| 78077365 | 6/1978 | Japan . |

OTHER PUBLICATIONS

*J. Am. Chem. Soc.*, 76 (1954) pp. 4382–4385.
*Hoppe–Seylers Z. Physiol. Chemie.*, 279 (1943) pp. 52–59.
*Chem. Ztg.*, 98 (1974) pp. 617–618.
*Chem. Ber.*, 33 (1900), pp. 1517–1519.

*Primary Examiner*—Joseph K. McKane
*Attorney, Agent, or Firm*—Keil & Weinkauf

[57] ABSTRACT

Substituted guanidine derivatives of the formula I,

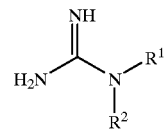

are prepared by a) reacting calcium cyanamide with an alcohol of the formula $R^{10}$—OH to give an isourea derivative of the formula II,

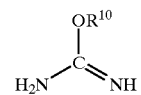

and b) reacting the substituted isourea with a primary or secondary amine of the formula III,

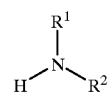

where the substituents $R^1$ and $R^2$ and $R^{10}$ have the meanings explained in the description.

8 Claims, No Drawings

PREPARATION OF SUBSTITUTED GUANIDINE DERIVATIVES

The present invention relates to a process for preparing substituted guanidinium compounds by reacting calcium cyanamide with alcohols to give isourea derivatives and reaction thereof with primary or secondary amines to give substituted guanidinium compounds.

Substituted guanidinium compounds are widespread in nature. Important representatives of this class of substances are, for example, amino acids such as arginine and creatine. In addition, substituted guanidine compounds are known as sterically hindered bases, as biocides and as complex ligands. However, the industrial applicability of most of the compounds of this type is greatly restricted owing to the high costs of their preparation.

One example of a biologically active guanidine derivative is creatine which, as the cell's energy carriers, is employed for dietary supplementation in the food and drugs sectors.

The preparation of creatine is described, for example, in EP-A-0 754 679 and the further literature quoted therein, the maximum yields obtained being only 70%.

One disadvantage of the abovementioned syntheses of guanidinium compounds is the use of aqueous solutions of pure cyanamide. These solutions are very costly and, because of the instability of cyanamide, generally not widely available.

The synthesis of guanidinium salts from pure O-alkylisourea derivatives is described by R. B. Fearing and S. W. Fox in J. Am. Chem. Soc. 76 (1954) 4382–4385.

The reaction of sarcosine with O-methylisourea hydrochloride, described by E. Schütte in Hoppe-Seylers Z. Physiol. Chemie 279 (1943) 52–59, affords creatine in a yield of only 21%.

JP 077364 describes the reaction of a solution of sodium sarcosinate with O-methylisourea methyl sulfate at pH 11 to give creatine.

It is a feature common to the abovementioned guanidinium syntheses that pure starting materials are used.

The preparation of O-alkylisoureas by acid-catalyzed reaction of anhydrous cyanamide with alcohols has been described (H. Krommer, Chem. Ztg. 98 (1974) 617–618; J. Stieglitz, R. H. McKee, Chem. Ber. 33 (1900) 1517–1519).

One disadvantage of this reaction is the use of anhydrous cyanamide which is costly and not readily available.

Another possibility for preparing O-alkylisoureas comprises reacting urea with dialkyl sulfates. Thus, JP 78-77365 describes the synthesis of O-methylisourea by alkylating urea with dimethyl sulfate.

A disadvantage of the alkylation of urea is the low selectivity of the reaction, i.e. the formation of byproducts such as N-alkyl derivatives and polyalkylated urea compounds.

It is an object of the present invention to provide a low-cost and straightforward process for preparing substituted guanidines based on widely available starting materials and not having the abovementioned disadvantages.

We have found that this object is achieved by a process for preparing substituted guanidine derivatives of the formula I,

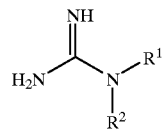

where the substituents $R_1$ and $R_2$ have the following meanings independently of one another:

$R^1$ H,
  $C_1$–$C_{20}$-alkyl, $C_2$–$C_{10}$-alkenyl, $C_3$–$C_8$-cycloalkyl;

$R^2$
  $C_1$–$C_{20}$-alkyl, $C_2$–$C_{10}$-alkenyl, $C_3$–$C_8$-cycloalkyl, —($C_1$–$C_{20}$-alkylene)—$COOR^3$, —($C_1$–$C_{20}$-alkylene)—$CONR^4R^5$, —($C_1$–$C_{20}$-alkylene)—CN, —($C_1$–$C_{20}$-alkylene)—$SO_2R^6$, —[($CH_2$)$_m$—X—]$_p$—[($CH_2$)$_n$—Y—]$_q$—[($CH_2$)$_o$]$_r$—Z;

m, n, o
  0 to 10;

p, q, r
  0 to 50,000;

X O, NH;

Y N—[($CH_2$)$_m$—X—]$_p$—[($CH_2$)$_n$—Y—]$_q$—[($CH_2$)$_o$]$_r$—Z;

Z OH, $NH_2$;

$R^3$ H, $C_1$–$C_{20}$-alkyl, $C_2$–$C_{10}$-alkenyl, $C_3$–$C_8$-cycloalkyl, $C_6$–$C_8$-aryl, Na, K, Li, Ca, Mg, $N(R^7)_4$;

$R^4$ and $R^5$ independently of one another
  H, $C_1$–$C_{20}$-alkyl, $C_2$–$C_{10}$-alkenyl, $C_{3\text{-}8}$a-cycloalkyl, $C_6$–$C_{18}$-aryl;

$R^6$ $OR^8$, $N(R^9)_2$;

$R^7$ H, $C_1$–$C_{20}$-alkyl;

$R^8$ H, $C_1$–$C_{20}$-alkyl, $C_2$–$C_{10}$-alkenyl, $C_3$–$C_8$-cycloalkyl, $C_6$–$C_{18}$-aryl, Na, K, Li, Ca, Mg, $N(R^7)_4$;

$R^9$ H, $C_1$–$C_{20}$-alkyl, $C_2$–$C_{10}$-alkenyl, $C_3$–$C_8$-cycloalkyl, $C_6$–$C_{18}$-aryl; which comprises a) reacting calcium cyanamide with an alcohol of the formula $R^{10}$-OH to give an isourea derivative of the formula II,

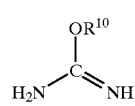

where $R^{10}$ can be $C_1$–$C_{20}$-alkyl, b) reacting the substituted isourea II with a primary or secondary amine of the formula III,

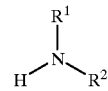

where the substituents $R^1$ and $R^2$ have the abovementioned meanings, to give the substituted guanidine compounds of the formula I.

The novel process satisfies in particular commercial limiting conditions such as low costs of starting materials, easy industrial implementation, improved yields and adequate purity of the product.

The novel process is particularly distinguished by the possibility of employing in the first stage, i.e. for preparing O-alkylisoureas, in place of the costly pure cyanamide, which is normally commercially available as crystalline pure product or as a solution stabilized at pH 3–6, the very low-cost and widely available nitrolime.

Nitrolime means products which are obtained, for example, by reacting $CaC_2$ with $N_2$ at 800–1100° C. As a rule, they contain 5–98% by weight, preferably 20–95% by weight, particularly preferably 30–90% by weight, of calcium cyanamide. The industrially available gray to black nitrolime contains not only calcium cyanamide but also impurities such as carbon, calcium carbide, CaO and traces of metals, normally in contents <1%. It is, of course, also possible to use pure calcium cyanamide. However, it is particularly advantageous, because more economical, to use technical, not very pure nitrolime. This is preferably employed in the form of a powder with a particle size distribution from 1 to 100 μm. However, it is also possible to employ granulated, extruded or otherwise compacted material, as well as an appropriate suspension in water, alcohols or other water-miscible solvents.

The substituted isourea derivatives of the first stage of the synthesis can be prepared by adding nitrolime to a mixture of 1 to 10 equivalents, preferably 2 to 8 equivalents, particularly preferably 3 to 5 equivalents, of mineral acid, preferably HCl, $H_2SO_4$ and $H_3PO_4$, and 1 to 10 equivalents, preferably 1.5 to 5 equivalents, of an alcohol of the formula $R^{10}$-OH.

In the case of the mineral acids, it is also possible to use, in particular, mixtures such as hydrochloric acid/sulfuric acid or hydrochloric acid/phosphoric acid in a ratio of 20/1 to 5/1, in particular 15/1 to 8/1. These mixtures have the advantage that heavy metals present in the reaction mixture are simultaneously precipitated.

Suitable alcohols of the formula $R^{10}$-OH are those where $R^{10}$ can be branched or unbranched $C_1$–$C_{20}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

Particularly preferred alcohols are aliphatic alcohols having 1 to 4 carbon atoms, e.g. methanol, ethanol, 1-propanol, 2-propanol, 1-butanol, 2-butanol, isobutanol.

To remove dissolved heavy metal ions, it may be advantageous to employ complexing agents such as phosphates, sulfates, aminopolycarboxylates, for example EDTA, or aminopolyphosphonates in amounts from 0.1 to 5 mol %, based on the calcium cyanamide used.

To eliminate odoriferous byproducts, it is additionally possible to add oxidizing agents such as $H_2O_2$.

It is possible in this way to improve the purity of the isourea derivative which is formed, without losses of yield.

The addition of nitrolime takes place in equal portions over a period of from 0.5 to 10 h, preferably from 1 to 6 h, particularly preferably from 2 to 5 h.

The metering in can take place in solid form or in the form of an alcoholic suspension.

The reaction in this case is carried out at from −20 to 60° C., preferably from −10 to 40° C., in particular from 0 to 25° C.

The metering is, as a rule, followed by stirring for 0.5 to 10 h, preferably 1 to 5 h.

Any inorganic byproducts precipitated in this stage can be removed at from 20 to 100° C., preferably 50 to 90° C., by processes known per se, such as filtration or centrifugation.

The isourea derivative which is formed can be reacted without further purification with primary or secondary amines in a second stage of the process to give substituted guanidine compounds.

All claimed amines of the formula III are suitable in principle for the reaction with the isourea derivatives of the formula II. These may be both aliphatic or cycloaliphatic primary or secondary amines, and amino carboxylic acids and amino sulfonic acids and their derivatives. It is also possible to react in the novel process primary and secondary amines which contain additional amino or imino groups, and amino-containing oligomers and polymers.

Alkyl radicals which may be mentioned for $R^1$ to $R^5$ and for $R^7$ to $R^9$ are branched or unbranched $C_1$–$C_{20}$-alkyl chains, preferably methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl or n-eicosyl.

Alkenyl radicals which may be mentioned for $R^1$ to $R^5$ and for $R^8$ and $R^9$ are branched or unbranched $C_2$-$C_{10}$-alkenyl chains, preferably vinyl, propenyl, isopropenyl, 1-butenyl, 2-butenyl, 1-pentenyl, 2-pentenyl, 2-methyl-1-butenyl, 2-methyl-2-butenyl, 3-methyl-1-butenyl, 1-hexenyl, 2-hexenyl, 1-heptenyl, 2-heptenyl, 1-octenyl or 2-octenyl.

Alkylene radicals which may be mentioned for $R^2$ are branched or unbranched $C_1$–$C_{20}$-alkylene chains, preferably methylene, ethylene, n-propylene, 1-methylethylene, n-butylene, 1-methylpropylene, 2-methylpropylene, 1,1-dimethylethylene, n-pentylene, 1-methylbutylene, 2-methylbutylene, 3-methylbutylene, 2,2-dimethylpropylene, 1-ethylpropylene, n-hexylene, 1,1-dimethylpropylene, 1,2-dimethylpropylene, 1-methylpentylene, 2-methylpentylene, 3-methylpentylene, 4-methylpentylene, 1,1- dimethylbutylene, 1,2-dimethylbutylene, 1,3-dimethylbutylene, 2,2-dimethylbutylene, 2,3-dimethylbutylene, 3,3-dimethylbutylene 1-ethylbutylene, 2-ethylbutylene, 1,1,2-trimethyl propylene, 1,2,2-trimethylpropylene, 1-ethyl-1-methylpropylene, 1-ethyl-2-methylpropylene, n-heptylene, n-octylene, n-nonylene, n-decylene, n-undecylene, n-dodecylene, n-tridecylene, n-tetradecylene, n-pentadecylene, n-hexadecylene, n-heptadecylene, n-octadecylene, n-nonadecylene or n-eicosylene.

The 1- to 20-membered alkylene chains may be substituted by the following radicals:

$C_1$–$C_6$-alkyl, for example methyl, ethyl, n-propyl, 1-methylethyl, n-butyl, 1-methylpropyl, 2-methylpropyl, 1,1-dimethylethyl, n-pentyl, 1-methylbutyl, 2,-methylbutyl, 3-methylbutyl, 2,2-dimethylpropyl 1-ethylpropyl, n-hexyl 1,1-dimethylpropyl, 1,2-trimethylpropyl 1y-methylpentyl 2-methylpentyl, 3-methylpentyl 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl;

mercaptomethyl, 1-aminobutyl, 1-carboxyethyl;

arylalkyl, for example benzyl, p-hydroxybenzyl, indolylmethyl.

Cycloalkyl radicals which may be mentioned for $R^1$ to $R^5$ and for $R^8$ and $R^9$ are branched or unbranched $C_3$–$C_8$-cycloalkyl radicals, preferably cyclopropyl, cyclobutyl, cyclopentyl, cyclohexyl, cycloheptyl, 1-methylcyclopropyl, 1-ethylcyclopropyl, 1-propylcyclopropyl, 1-butylcyclopropyl, 1-pentylcyclopropyl, 1-methyl-1-butylcyclopropyl, 1,2-dimethylcyclopropyl, 1-methyl-2-ethylcyclopropyl or cyclooctyl.

The cycloalkyl radicals may be substituted by one or more, e.g. 1 to 3, radicals such as halogen, e.g. fluorine, chlorine or bromine, cyano, nitro, amino, $C_1$–$C_4$-alkylamino, $C_1$–$C_4$-dialkylamino, hydroxyl, $C_1$–$C_4$-alkyl, $C_1$–$C_4$-alkoxy or other radicals, or contain 1 to 3 heteroatoms such as sulfur, nitrogen, whose free valences can be saturated by hydrogen or $C_1$–$C_4$-alkyl, or oxygen, in the ring.

Suitable alkoxy radicals for $R^6$ are those having 1 to 20 carbon atoms, preferably having 1 to 12 carbon atoms, particularly preferably having 1 to 8 carbon atoms.

Examples which may be mentioned are:

| | |
|---|---|
| methoxy | ethoxy- |
| isopropoxy- | n-propoxy- |
| 1-methylpropoxy- | n-butoxy- |
| n-pentoxy- | 2-methylpropoxy- |
| 3-methylbutoxy- | 1,1-dimethylpropoxy- |
| 2,2-dimethylpropoxy- | hexoxy- |
| 1-methyl-1-ethylpropoxy- | heptoxy- |
| octoxy- | 2-ethylhexoxy- |

Suitable and preferred mono- or disubstituted amino radicals for $R^6$ are those containing alkyl radicals having 1 to 20, preferably 1 to 12, carbon atoms, e.g. methyl, n-propyl, n-butyl, 2-methylpropyl, 1,1-dimethylpropyl, hexyl, heptyl, 2-ethylhexyl, isopropyl, 1-methylpropyl, n-pentyl, 3-methylbutyl, 2,2-dimethylpropyl, 1-methyl-1-ethylpropyl and octyl.

Suitable tetraalkylammonium radicals for $R^3$ and $R^8$ are those containing alkyl radicals having 1 to 20, preferably 1 to 12, particularly preferably 1 to 6, carbon atoms, e.g. methyl, n-propyl, isopropyl, 2-methylpropyl, 1,1-dimethylpropyl, 1-methylpropyl, 2,2-dimethylpropyl, 1-methyl-1-ethylpropyl, n-butyl, 3-methylbutyl, n-pentyl and hexyl.

Aryl means aromatic rings or ring systems having 6 to 18 carbon atoms in the ring system, for example phenyl or naphthyl, each of which may be substituted by one or more radicals such as halogen, e.g. fluorine, chlorine or bromine, cyano, nitro, amino, $C_1$–$C_4$-alkylamino, $C_1$–$C_4$-dialkylamino, hydroxyl, $C_1$–$C_4$-alkyl, $C_1$–$C_4$-alkoxy or other radicals. Unsubstituted or substituted phenyl, methoxyphenyl and naphthyl are preferred.

Amines which are preferably used are all primary and secondary amines which are soluble in water or in water-miscible solvents. Preferred representatives among the simple amines are, inter alia, methylamine, ethylamine, n-propylamine, 2-propylamine, butylamine, isobutylamine, aniline, benzylamine and anthranilic acid. Further amino-containing compounds which are preferably employed are, inter alia, taurine and amino carboxylic acids such as glycine, alanine, valine, proline, leucine, phenylalanine, lysine, methionine, cysteine, aspartic acid, iminodiacetic acid, sarcosine and their esters, amides and nitriles and their salts. Sarcosine is the very particularly preferred compound of the formula III and can be used both as free acid and, in particular, as Na or K salt in the form of a 5 to 60% by weight, preferably 35 to 45% by weight, aqueous solution.

It is also possible to employ water-soluble, amino-containing oligomers and polymers in the novel process, such as alkylenediamines, dialkylenetriamines and so on up to polyalkylenepolyamines or polyetherdiamines. Preferred representatives of this group are ethylenediamine, propylenediamine, butylenediamine, hexamethylenediamine, diethylenetriamine, triethylenetetramine, tetraethylenepentamine, pentaethylenehexamine, hexaethyleneheptamine and branched or linear polyalkylenepolyamines.

Suitable and preferred polyalkylenepolyamines are polyethyleneimines which have, for example, molecular weights of from 200 to 10 million, preferably 1000 to 3 million. Polyethyleneimines with molecular weights of from 2000 to 1,300,000 are particularly preferably employed.

The polyetherdiamines are prepared, for example, by reacting polyalkylene glycols with ammonia. The polyalkylene glycols may contain 2 to 50, preferably 2 to 40, alkylene oxide units. These may be, for example, polyethylene glycols, polypropylene glycols, polybutylene glycols or else block copolymers of ethylene glycol and propylene glycol, block copolymers of ethylene glycol and butylene glycol or block copolymers of ethylene glycol, propylene glycol and butylene glycol. Apart from the block copolymers, also suitable for preparing polyetherdiamines are random copolymers of ethylene oxide and propylene oxide with or without butylene oxide. Polyetherdiamines are also derived from polytetrahydrofurans having 2 to 75 tetrahydrofuran units. The polytetrahydrofurans are likewise converted via reaction with ammonia into the corresponding α,ω-polyetherdiamines. Polyethylene glycols or block copolymers of ethylene glycol and propylene glycol are preferably used to prepare the polyetherdiamines.

Further suitable amino-containing water-soluble polymers are polyvinylamines which are obtainable by homo- and/or copolymerization of N-vinylformamide and subsequent hydrolysis of the polymers, and polymers containing vinylamine units. Substances of this type are known, cf. EP-B-0 071 050 and EP-B-0 216 387. Suitable and preferred polymers are hydrolyzed homopolymers of N-vinylformamide having a degree of hydrolysis of from 1 to 100, preferably 80 to 100, % and partially or completely hydrolyzed copolymers of N-vinylformamide and vinyl formate or vinyl acetate. The N-vinylformamide units in the copolymers are preferably 80 to 100% hydrolyzed. Depending on the hydrolysis conditions, the monomer units such as vinyl formate or vinyl acetate can be partially or completely hydrolyzed to vinyl alcohol units. Further comonomers suitable for preparing hydrolyzed copolymers of N-vinylformamide are monoethylenically unsaturated carboxylic acids such as acrylic acid, methacrylic acid or maleic acid, N-vinylpyrrolidone and acrylonitrile.

Further amino-containing water-soluble polymers are polyallylamines. These polymers contain at least 3 allylamine units and have molecular weights of up to 10 million.

The use of technical products is particularly advisable when no other unwanted reactive amines are present in the mixture and it is particularly advantageous for economic reasons, for example the purification of the amine is costly and complicated.

Reaction of the substituted isourea derivatives with the abovementioned amines can take place in water or a water-miscible solvent or a mixture thereof. The pH normally used in this case is in the region of the pK of the amine, i.e. at a pH of from 6 to 14, preferably from 8 to 12, particularly preferably from 9 to 11.

The molar ratio of substituted isourea derivatives to primary or secondary amine is in the range from 0.9 to 5.0, preferably from 1.0 to 2.0.

The reaction in the second stage is carried out at from −20 to 100° C., preferably from 0 to 60° C., particularly preferably from 10 to 40° C.

The sequence of addition of the reactants for the reaction in the second stage of the process is not particularly important. As a rule, the substituted isourea is added to the primary or secondary amine, which can preferably be in aqueous or alcoholic solution.

The addition can extend over a period of from 0.5 to 10 h, preferably from 1 to 3 h.

The pH can be maintained by employing, depending on the initial pH of the base, either acids such as $CO_2$, $SO_2$, HCl, $HNO_3$, $H_2SO_4$, $H_2SO_3$, $H_3PO_3$, $H_3PO_2$ and $H_3PO_4$, and/or bases such as NaOH, KOH, LiOH, $Ca(OH)_2$, $Ba(OH)_2$, $Mg(OH)_2$. Only acids are required if the amines should be present in basic and not in neutralized or partially neutralized form.

Preferred acids are those which are easily available industrially and result together with traces of heavy metals in complexes of low solubility, such as $CO_2$, $H_2SO_4$, $H_3PO_4$. However, it is also possible and preferred to employ mixtures of these and other acids.

After removal of the complexed byproducts which have precipitated where appropriate, either by hot filtration or centrifugation, the required guanidinium derivatives are isolated in a manner known per se. Thus, the required product can be obtained as crystals, for example, by cooling the filtered reaction solution to −20 to 60° C., in particular 0 to 40° C.. After filtration, the purity can be improved where appropriate by a recrystallization. However, it is also possible to remove the product from the reaction mixture by extraction and then to isolate it pure by distillation or crystallization.

It is particularly surprising that the yields of the novel reaction based on the content of cyanamide (1st stage) and O-alkylisourea (2nd stage) are comparable on use of the technical starting materials and when pure cyanamide and O-alkylisoureas are reacted. Taking account of the purification step for preparing pure cyanamide and O-alkylisourea, the yield is far higher because of the smaller number of steps in the process.

In addition, even higher conversions can be achieved by employing the low-cost isourea compound in excess relative to the amine in the second step of the process, which is frequently uneconomical on use of pure cyanamide or pure O-alkylisourea. The purity of the isolated guanidinium salt is comparable with that prepared from pure cyanamide. This is attributable in particular to the high purity of the isourea derivatives obtained according to the invention.

The process for preparing substituted guanidinium derivatives is explained in detail in the following example.

EXAMPLE

Preparation of creatine

Stage 1: Synthesis of O-methylisourea hydrochloride 400 ml of dry methanol and 1 ml of 85% strength phosphoric acid in a 500 ml round-bottomed flask with stirrer, gas-introduction tube, reflux condenser and drying tube were saturated with dry hydrogen chloride gas at 0 to 5° C. Then, while cooling in ice, 120 g of nitrolime with a $CaCN_2$ content of 43% by weight were introduced in such a way that the temperature did not exceed 20° C. The addition was followed by stirring at 20° C. for 2 h. The reaction mixture was then refluxed, the suspension formed was filtered, and the filter cake was washed three times with 50 ml of methanol each time. The combined mother liquors were concentrated to 200 ml under reduced pressure. HPLC analysis showed that the concentrate contained 61.2 g of O-methylisourea hydrochloride, corresponding to a yield of 88%.

Stage 2: Reaction of O-methylisourea hydrochloride with sarcosine

The methanolic O-methylisourea hydrochloride solution prepared in the first stage was metered over the course of 2 h into a mixture of 138 g of 40.1% by weight aqueous sodium sarcosinate solution, 16.2 g of 50% by weight sulfuric acid and 53 g of water at pH 11 and 20° C. The pH was kept at 11 during the addition by simultaneous addition of 20% by weight NaOH. After the addition was complete, the mixture was stirred at 20° C. for 6 h and then the solvent was removed by distillation under reduced pressure at 60° C. until about 150 ml were left. Crystallization of the residue resulted in 62.5 g of creatine with a purity of 88% and a residual water content of 12%. Analysis of the mother liquor showed that the total yield of creatine in the reaction was 87%.

We claim:

1. A process for preparing substituted guanidine compounds of the formula I,

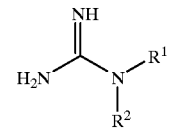

where the substituents have the following meanings independently of one another:

$R^1$ H,
  $C_1$–$C_{20}$-alkyl, $C_2$–$C_{10}$-alkenyl, $C_3$–$C_8$-cycloalkyl;

$R^2$ $C_1$–$C_{20}$-alkyl, $C_2$–$C_{10}$-alkenyl, $C_3$–$C_8$-cycloalkyl,
  —($C_1$–$C_{20}$-alkylene)—$COOR^3$,
  —($C_1$–$C_{20}$-alkylene)—$CONR^4R^5$, —($C_1$–$C_{20}$-alkylene)—CN,
  —($C_1$–$C_{20}$-alkylene)—$SO_2R^6$,
  —[$(CH_2)_m$—X—]$_p$—[$(CH_2)_n$—Y—]$_q$—[$(CH_2)_o$]$_r$—Z;

m, n, o
  0 to 10;

p, q, r
  0 to 50,000;

X O, NH;

Y N—[$(CH_2)_m$—X—]$_p$—[$(CH_2)_n$—Y—]$_q$—[$(CH_2)_o$]$_r$—Z;

Z OH, $NH_2$;

$R^3$ H, $C_1$–$C_{20}$-alkyl, $C_2$–$C_{10}$-alkenyl, $C_3$–$C_8$-cycloalkyl, $C_6$–$C_{18}$-aryl
  Na, K, Li, Ca, Mg, $N(R^7)_4$;

$R^4$ and $R^5$ independently of one another
  H, $C_1$–$C_{20}$-alkyl, $C_2$–$C_{10}$-alkenyl, $C_3$–$C_8$-cycloalkyl, $C_6$–$C_{18}$-aryl;

$R^6$ $OR^8$, $N(R^9)_2$;
$R^7$ H, $C_1$–$C_{20}$-alkyl;
$R^8$ H, $C_1$–$C_{20}$-alkyl, $C_2$–$C_{10}$-alkenyl, $C_3$–$C_8$-cycloalkyl, $C_6$–$C_{18}$-aryl,
    Na, K, Li, Ca, Mg, $N(R^7)_4$;
$R^9$ H, $C_1$–$C_{20}$-alkyl, $C_2$–$C_{10}$-alkenyl, $C_3$–$C_8$-cycloalkyl, $C_6$–$C_{18}$-aryl;
which comprises
  a) reacting calcium cyanamide with an alcohol of the formula $R^{10}$-OH to give an isourea compound of the formula II,

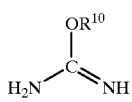

II where $R^{10}$ can be $C_1$–$C_{20}$-alkyl,
  b) reacting the substituted isourea II with a primary or secondary amine of the formula III,

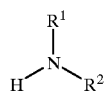

III where the substituents $R^1$ and $R^2$ have the abovementioned meanings, to give guanidine compounds of the formula I.

2. A process as claimed in claim 1, wherein calcium cyanamide is reacted in step a) with an alcohol of the formula $R^{10}$—OH at from −20 to 60° C. in the presence of mineral acids.

3. A process as claimed in claim 1, wherein calcium cyanamide is used in step a) in the form of technical nitrolime with a calcium cyanamide content of from 30 to 95% by weight.

4. A process as claimed in claim 1, wherein step b) is carried out at from −20 to 100° C. and at a pH of from 6 to 14.

5. A process as claimed in claim 1, wherein the substituted isourea compounds are employed in step b) directly from stage a) without isolation.

6. A process as claimed in claim 1, wherein an amine which is soluble in water or in a water-miscible solvent is used as primary or secondary amine of the formula III in step b).

7. A process as claimed in claim 6, wherein a primary or secondary amine selected from the group of amino carboxylic acids, their esters, amides and nitrites, and amino sulfonic acids and their esters and amides is used.

8. A process as claimed in claim 6, wherein a primary or secondary amine selected from the group of alkylenediamines, dialkylenetriamines, trialkylenetetramines and polyalkylenepolyamines is used.

* * * * *

UNITED STATES PATENT AND TRADEMARK OFFICE
CERTIFICATE OF CORRECTION

PATENT NO.: 5,969,182

DATED: October 19, 1999

INVENTOR(S): GREINDL et al.

It is certified that error appears in the above-identified patent and that said Letters Patent is hereby corrected as shown below:

Col. 10, claim 7, line 22, "nitrites" should be --nitriles--.

Signed and Sealed this

Eighteenth Day of April, 2000

Attest:

Q. TODD DICKINSON

*Attesting Officer*    *Director of Patents and Trademarks*